US009700738B2

(12) United States Patent
Martin et al.

(10) Patent No.: US 9,700,738 B2
(45) Date of Patent: *Jul. 11, 2017

(54) SYSTEM AND COMPUTER PROGRAM PRODUCT FOR RADIATION INVERSE TREATMENT PLANNING

(71) Applicant: Intuitive Therapeutics SA, Sion (CH)

(72) Inventors: Andre Martin, Preverenges (CH); Daniel Salzmann, Saint Prex (CH)

(73) Assignee: Intuitive Therapeutics SA (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/317,149

(22) Filed: Jun. 27, 2014

(65) Prior Publication Data

US 2015/0360052 A1    Dec. 17, 2015

(30) Foreign Application Priority Data

Jun. 17, 2014   (CH) ...................................... 0914/14
Jun. 17, 2014   (CH) ...................................... 0915/14

(51) Int. Cl.
*A61N 5/10*          (2006.01)
*G06F 17/16*         (2006.01)
(Continued)

(52) U.S. Cl.
CPC ........... *A61N 5/1031* (2013.01); *A61N 5/103* (2013.01); *A61N 5/1075* (2013.01);
(Continued)

(58) Field of Classification Search
CPC .... A61N 5/103; A61N 5/1031; A61N 5/1037; A61N 5/1042; A61N 5/1064;
(Continued)

(56) References Cited

U.S. PATENT DOCUMENTS

2006/0274885 A1*  12/2006  Wang ..................... G06Q 50/22
                                                              378/65
2006/0274925 A1   12/2006  West et al.
(Continued)

FOREIGN PATENT DOCUMENTS

WO    WO-2009137010 A2    11/2009

OTHER PUBLICATIONS

Hyder et al., An approximate L0 norm minimization algorithm for compressed sensing, Apr. 2009, IEEE Intl. Conf. Acoustics, Speech and Signal Processing (ICASP), p. 3365, 3366.*

(Continued)

*Primary Examiner* — Anastasia Midkiff
(74) *Attorney, Agent, or Firm* — Blank Rome LLP

(57) ABSTRACT

The present invention concerns a radiation inverse treatment planning system for a linear accelerator. The system includes a radiation source, configured for delivering individual radiotherapeutic dose shots (aj), each individual radiotherapeutic dose shot having a predetermined location and incidence angle inside and/or outside a target area, a size and a shape. The system also includes at least a data bus system (102), and a memory (106) coupled to the data bus system (102), wherein the memory (106) includes a computer usable program code. The system also includes a processing unit (104) coupled to the data bus system (102), wherein the processing unit (104) is configured to execute the computer usable program code to pre-compute (10) a set of individual radiotherapeutic dose shots (aj), and associate (40) a weight (sj) to each individual radiotherapeutic dose shot (aj), based on one or more constraints (20). The processing unit (104) executes the computer usable program code to find (30) the sparsest subset of individual radiotherapeutic dose shots, so as to satisfy said one or more constraints (20).

21 Claims, 2 Drawing Sheets

(51) Int. Cl.
*G01T 1/29* (2006.01)
*A61B 6/00* (2006.01)
*G06F 17/30* (2006.01)

(52) U.S. Cl.
CPC ...... *G06F 17/30271* (2013.01); *A61B 6/5294* (2013.01); *A61B 6/54* (2013.01); *A61N 5/1038* (2013.01); *A61N 5/1042* (2013.01); *A61N 5/1047* (2013.01); *A61N 5/1071* (2013.01); *G01T 1/2914* (2013.01); *G05B 2219/33079* (2013.01); *G06F 17/16* (2013.01)

(58) Field of Classification Search
CPC .. A61N 5/1071; A61N 5/1081; A61N 5/1083; A61N 5/1084; A61N 5/00; A61N 5/10; A61N 5/1038; A61N 5/1039; A61N 5/1047; A61N 5/1075; A61N 2005/0626–2005/0628; A61B 6/00; A61B 6/52; A61B 6/5205; A61B 6/5211; A61B 6/5294; A61B 6/54; G05B 2219/34017; G05B 2219/33079; G06F 7/52; G06F 7/78; G06F 9/00; G06F 9/30; G06F 9/30003; G06F 9/30007; G06F 9/30036; G06F 15/8053; G06F 15/76; G06F 15/80; G06F 17/00; G06F 17/10; G06F 17/16; G06F 17/30244; G06F 17/30271; G01T 1/1663; G01T 1/2992; G01T 1/2914; G01T 1/29; G01T 1/2928; G01T 1/2964; G01T 1/2971; G01T 1/2978; G01T 1/2985
See application file for complete search history.

(56) References Cited

U.S. PATENT DOCUMENTS

| | | | |
|---|---|---|---|
| 2009/0154644 A1* | 6/2009 | Nord | A61N 5/103 378/65 |
| 2011/0085643 A1* | 4/2011 | Zhu | A61N 5/1031 378/65 |
| 2011/0091014 A1* | 4/2011 | Siljamaki | A61N 5/1031 378/65 |
| 2013/0188856 A1 | 7/2013 | Adler, Jr. et al. | |
| 2013/0346082 A1 | 12/2013 | Aly et al. | |

OTHER PUBLICATIONS

K. S. Clifford Chao, et al., "Practical Essentials of Intensity Modulated Radiation Therapy", Second Edition, Lippincott Williams & Wilkins, 2005, 3 pages.

Y. Zhang, et al., "Fluence Map Optimization in IMRT Cancer Treatment Planning and A Geometric Approach", Jul. 2004, pp. 1-22.

"Radiation Oncology", IMRT/Radiation Oncology, http://radiationoncology.weillcornell.org/clinical-services-and-technologies/external...etc.: pp. 1-3.

Hansen VN, et al., "Quality Assurance of the Dose Delivered by Small Radiation Segments", Phys. Med. Biol.; Joint Department of Physics, Royal Marsden Trust NHS Trust and Institute of Cancer Research, Sutton, Surrey, UK; Sep. 1998; vol. 43, No. 9, pp. 2665-2675.

* cited by examiner

SYSTEM AND COMPUTER PROGRAM PRODUCT FOR RADIATION INVERSE TREATMENT PLANNING

REFERENCE DATA

The present application claims the priority of Swiss Patent Application CH0915/14, filed on Jun. 17, 2014, the content of which is incorporated here by reference, and of the of Swiss Patent Application CH0914/14, filed on Jun. 17, 2014, the content of which is incorporated here by reference.

FIELD OF THE INVENTION

The present invention relates to a system and a computer program product for radiation inverse treatment planning, e.g. and in a non-limiting way for a linear accelerator (LINAC).

DESCRIPTION OF RELATED ART

Many radiation therapy systems, including radiotherapy and radiosurgery systems, use so-called linear accelerators (LINAC) which produce a single radiation beam, to irradiate a target region of the body.

The radiation beam of a linear accelerator is a single beam, which can be modelled by different types of collimator systems that allow to collimate the size of the beam. The "Gamma Knife®" uses a plurality of beams, e.g. about 200 beams, which focus on the same area, delivered in one session, which is the principle of radiosurgery.

The area irradiated by the single radiation beam of a linear accelerator has generally a diameter higher that the area irradiated by the "Leksell Gamma Knife®" or simply "Gamma Knife®", a tool commonly used for treating intracranial diseases. For example, the area irradiated by the single radiation beam of a linear accelerator has a diameter belonging to the range 10 cm-30 cm, e.g. 20 cm; the area irradiated by the "Gamma Knife®" has a precise diameter 4, 8, or 16 mm, depending on the size of collimators selected. Some linear accelerators for radiosurgery are equipped with micro multi-leafs collimators that can produce a single radiation beam having a diameter belonging to the range of few millimeters.

In most instances, the irradiation of a linear accelerator is performed not only under one single incidence (i.e. one shot), corresponding to a fixed pre-determined position and orientation of the radiation beam with respect to the target, but it uses multiple successive incidences to increase the conformity of the dose delivery. A large number of multiple incidences is used to perform the so-called Linac-based radiosurgery.

In most of the LINAC-based radiotherapy systems, the emission head is attached to a physical support (called the "gantry") that can be mechanically rotated around the patient, in a full or partial circle. The table where the patient is lying (called the "couch"), can sometimes also be moved in small linear or angular steps.

The combination of the movements of the gantry and/or of the couch makes possible the intersection of multiple successive radiation beams at the target location (at the so-called isocenter), thus producing a high total dose inside the target and at the same time, resulting in lower radiation in the surrounding areas.

Some other systems, namely the Cyberknife, commercialized by the company Accuray, uses a small-size LINAC mounted on a robotic arm, allowing large freedom in the motion of the robot head holding the LINAC, and thus allowing a large variety of the LINAC locations and incidence angles.

In all those systems, a planning phase is necessary to determine, in the most general case, the number, location, incidence angle, shape and weight of the successive irradiation shots in order to deliver the desired dose profile to the target region while, if necessary, protecting surrounding sensitive regions from a too high irradiation dose.

In the context of the present invention, a shot (or dose shot) is then a radiation dose delivered from a given location, incidence angle, with a given shape and weight. A treatment session can comprise a plurality of shots of different sizes and shapes.

Depending on the type of system, the parameters to be defined may be more restricted than those described above. As an example, when the LINAC is mounted on a rotating gantry with a fixed couch, the set of incidence angles is restricted to those produced by the rotation of the gantry.

Similarly, depending on the system, the shape of the irradiation beam can be set by fixed or variable size collimators, or by adaptive shape collimators, such as the so-called multi-leaf collimators.

For each shot, the user, i.e. the doctor(s) and/or the physicist, has to determine its location and incidence angle in the target area, as well as the size and shape of the irradiation dose to be delivered around the isocentre.

For each shot, the user has also to determine the time of irradiation in relation of the dose-rate of the sources (i.e. the time during which the LINAC is working). In the most advanced current systems, such as VMAT (Elekta), and RapidArc (Varian), the user has to determine the dose rate (i.e. the amount of radiation per unit of time). In other system, the user has to determine other parameters of the shot, e.g in a non-limiting way, the profile of the irradiation in the dose's area (e.g. a Gaussian profile, a flat profile, etc.).

In the context of the present invention, the noun "weight" refers to one or more parameters of the shot, e.g. in a non-limiting way, the time of irradiation and/or the dose rate and/or the dose profile, etc.

In the planning phase, each patient's treatment plan is generally developed by a radio-oncologist working in conjunction with a physicist. According to the most widely used planning procedure, they determine, through an iterative process of trial and error, the number, location and incidence angle of shots, along with their size, shape, and weight, and most recently dose rate.

Known radiation inverse treatment planning systems for LINACs calculate the number, location and incidence angle of shots, along with their size, shape, and weight, and most recently dose rate, only once. Moreover, some treatment systems use sensors in or on the patient for taking into account of the movements of the patient when delivering the radiation, e.g. as the patient breathes, or of one or more moving organs of the patient. However the know systems are not able to perform a real-time calculation of the shots, so as to adapt them to these movements.

Known radiation inverse treatment planning systems are not sufficiently precise, so that the protection of the areas surrounding the target, e.g. a tumor, is not totally effective, especially in larger tumours. This requires a plurality of sessions of the radiation treatment, e.g. radiotherapy.

Moreover, the current procedure for the planning step is relatively complex, tedious, unintuitive and slow. The duration of the planning procedure decreases the productivity and increases the cost of every treatment. Moreover its quality depends essentially on the experience of the user. Acquiring this experience requires a long training period.

Indeed, the current way to do the planning requires to define technical parameters of the machine that will ultimately produce the desired dose distribution. The relationship between those parameters and the actual dose distribution is not always intuitive. The medical user is thus asked to acquire and exploit a technical expertise, and in most of the cases needs to be help by a medical physicist, while he/she should rather concentrate on the medical aspects of the treatment.

To help the user, automatic inverse planning systems have been proposed. The planning is "inverse" as, based on the knowledge of the target region properties (e.g. from CT or MRT images), the operator prescribes a certain dose distribution within the target region and/or certain dose constraints. An automatic inverse planning system finds a set of parameters resulting in a treatment planning which is as close as possible to the predetermined dose distribution.

The classic inverse planning procedure requires then the definition, by the operator, of the target area and the minimum dose that should be delivered to it. Secondarily, the planning system also helps to minimize the dose to the areas to be protected.

The inverse planning is then typically defined as an optimization problem where the technical parameters are automatically searched to minimize a cost function measuring the difference between the desired dose distribution and that actually achieved. Various optimization techniques may be used.

Such inverse planning systems are used today, but they are time consuming, as they use slow optimisation techniques and require, most of the time, some parts of manual definition of some parameters by a physicist. The process has then to be repeated if the medical oncologist considers that the final result is not optimal, requiring more work and time for the physicist team.

It is then an aim of the present invention to obviate or mitigate one or more of the aforementioned disadvantages.

It is an aim of the present invention to provide a radiation inverse treatment planning system, which can simplify the planning phase of a treatment.

It is an aim of the present invention to provide a radiation inverse treatment planning system able to perform a real-time calculation of the shots, so as to adapt them to the patient's movements.

It is an aim of the present invention to provide a radiation inverse treatment planning system more precise than the known system.

It is an aim of the present invention to provide a radiation inverse treatment planning system, which is an alternative to the existing systems.

BRIEF SUMMARY OF THE INVENTION

According to the invention, these aims are achieved by means of a radiation inverse treatment planning system, comprising:
- a radiation source, configured for delivering individual dose shots, each individual dose shot having a predetermined location and incidence angle inside and/or outside a target area, a size and a shape
- at least a data bus system,
- a memory coupled to the data bus system, wherein the memory comprises a computer usable program code, and
- a processing unit coupled to the data bus system, wherein the processing unit is configured to execute the computer usable program code to
  - pre-compute a set of individual dose shots,
  - associate a weight to each individual dose shot, based on one or several constraints.

In one embodiment, the weight associate to each individual dose shot comprises the time of irradiation.

In another embodiment, the weight associate to each individual dose shot comprises the dose rate.

In another embodiment, the weight associate to each individual dose shot comprises the dose profile.

In another embodiment, the weight associate to each individual dose shot comprises any other parameter of the dose shot.

The radiation inverse treatment planning system of the present invention can use a linear accelerator (LINAC) as a radiation source.

The radiation inverse treatment planning system of the present invention is not limited to the use of a linear accelerator (LINAC) as a radiation source, and can use any other type of radiation source, e.g. and in a non-limiting way cobalt sources or proton beams.

The present invention proposes an automated method for inverse planning radiation treatment system, where the complete dose distribution delivered is modelled as a sparse linear combination of beams chosen from a pre-defined dictionary. Advantageously the one or more constraints can be related to the corresponding resulting dose distribution.

Advantageously the weight may be representative of the time of irradiation of the single or individual dose shot.

The use of a sparsity criterion allows to eliminate a lot of solutions a priori not-possible, and then to quickly converge to a solution. The sparsity allows then computations in real-time, so that it is possible to perform a real-time calculation of the shots, so as to allow interactive planning and to adapt them to the movements of the patient and/or of an organ of the patient, and/or to the relative movement between the physical support of the radiation source (the gantry) and the physical support of the patient (the couch).

Moreover, the system according to the invention is more precise than the known system, allowing to define more intuitive constraints and to realize them, so that the protection of the areas surrounding the target, e.g. a tumor, is more effective. This may require few sessions of the radiation treatment, e.g. one to five sessions in radiosurgery, or a larger number of sessions in fractionated radiotherapy when indicated.

In a preferred embodiment, the system comprises
- a first physical support for this radiation source, e.g. the gantry
- a second physical support arranged for receiving a patient, e.g. the couch. The first physical support and the second physical support are arranged to be moved one relative to the other. Advantageously the processing unit executes the computer usable program code to
- find the sparsest subset of individual dose shots, so as to satisfy this one or more constraints each time that the first physical support is moved relatively to the second physical support and/or each time that the second physical support is moved relatively to the first physical support.

In another embodiment, the processing unit executes the computer usable program code to find the sparsest subset of individual dose shots, so as to satisfy this one or more constraints each time that a patient and/or an organ of the patient moves.

In a preferred embodiment, the constraint comprises at least the coverage of the whole of part of the target region by a desired dose distribution. Further constraints may be added to modify the dose distribution outside of the target volume, and to limit the maximal dose to defined structures. Constraints may also be added to define the dose distribution within the target volume, if desired.

According to the invention, the processing unit executes the computer usable program code to
  find the sparsest subset of shots so as to satisfy the constraint(s).

The inventive system according to the invention allows to drastically simplify the radio-surgical planning via real-time inverse planning system.

In a preferred embodiment, the processing unit executes the computer usable program code to find the minimum number of non-zero weights so as to satisfy said one or more constraints.

The inventive system according to the invention allows to calculate the optimal technical parameters of irradiation to achieve the constraints imposed on the dose distribution. Considering the number of parameters that can be defined by the user during a manual planning, the optimal solution is in practice almost impossible to find, especially in the treatment of complex shape targets, even by an experienced user.

The inventive system according to the invention allows the user to interactively define the constraints on the dose to be delivered, in coverage, magnitude and gradients at the edges of the target or anywhere else in the volume of interest.

The advantages for the user are at least the following:
  He/she does not have to concentrate on the technical aspect of the realization of the desired dose distribution, but only has to consider which dose he/she wants to administer, and where.
  The interactive planning tool allows him/her to decide and modify in real-time the shape of the dose distribution to ensure proper irradiation of the target and proper protection of other organs.
  The planning becomes intuitive, fast, and thus cost-effective.
  The user can also easily add more constraints on the problem, such as a maximal treatment duration, the system providing the best possible planning to be as close as possible to the desired dose distribution while remaining within the time budget, for example.

The planning procedure performed by the system according to the invention is much more simple, faster and more user friendly than the known solutions, especially in complex target configurations.

A convex constrained optimization problem can be used to determine the treatment plan, i.e. the number of beams as well as the beam orientations, sizes, shapes and weights (or a subset of those parameters, depending on the physical properties of the considered system), so as to produce a desired dose delivery profile.

The optimization problem can include dose constraints applied to both the target region and other areas such as sensitive structures to be protected against high radiation dose.

A dictionary composed by a large set of beams covering totally or partially the set of possible beam locations, incidence angles, sizes and shapes, can be computed. After this computation, a convex optimization problem can be solved to determine the optimal plan, i.e. the optimal subset of those beams as well as their amplitude, so as to meet the defined constraints.

The present invention concerns also a computer program product, comprising:
a tangible computer usable medium including computer usable program code for a radiation inverse treatment planning system comprising a radiation source configured for delivering individual dose shots, each individual dose shot having a predetermined location and incidence angle inside and/or outside a target area, a size and a shape, the computer usable program code being used for
  pre-compute a set of individual dose shots,
  associate a weight to each individual dose shot, based on one or more constraints, e.g. on the corresponding resulting dose distribution,
characterised in that the processing unit executes the computer usable program code to
  find the sparsest subset of individual dose shots, so as to satisfy said one or more constraints.

The present invention concerns also a computer data carrier storing presentation content created with a radiation inverse treatment planning method, comprising the following steps:
  pre-compute a set of individual dose shots, each individual dose shot being generated by a radiation source, and having a predetermined location and incidence angle inside and/or outside a target area, a size and a shape,
  associate a weight to each individual dose shot, based on one or several constraints, e.g. on the corresponding resulting dose distribution,
characterised in that the processing unit executes the computer usable program code to
  find the sparsest subset of individual dose shots, so as to satisfy said one or more constraints.

BRIEF DESCRIPTION OF THE DRAWINGS

The invention will be better understood with the aid of the description of an embodiment given by way of example and illustrated by the figures, in which.

DETAILED DESCRIPTION OF POSSIBLE EMBODIMENTS OF THE INVENTION

Although the present invention will be described in more detail in connection with a LINAC as radiation source, the present invention finds applicability of connection with many other sources, as explained here above. For example, it can use other radiation sources, as cobalt sources or proton beams.

Figure 1:
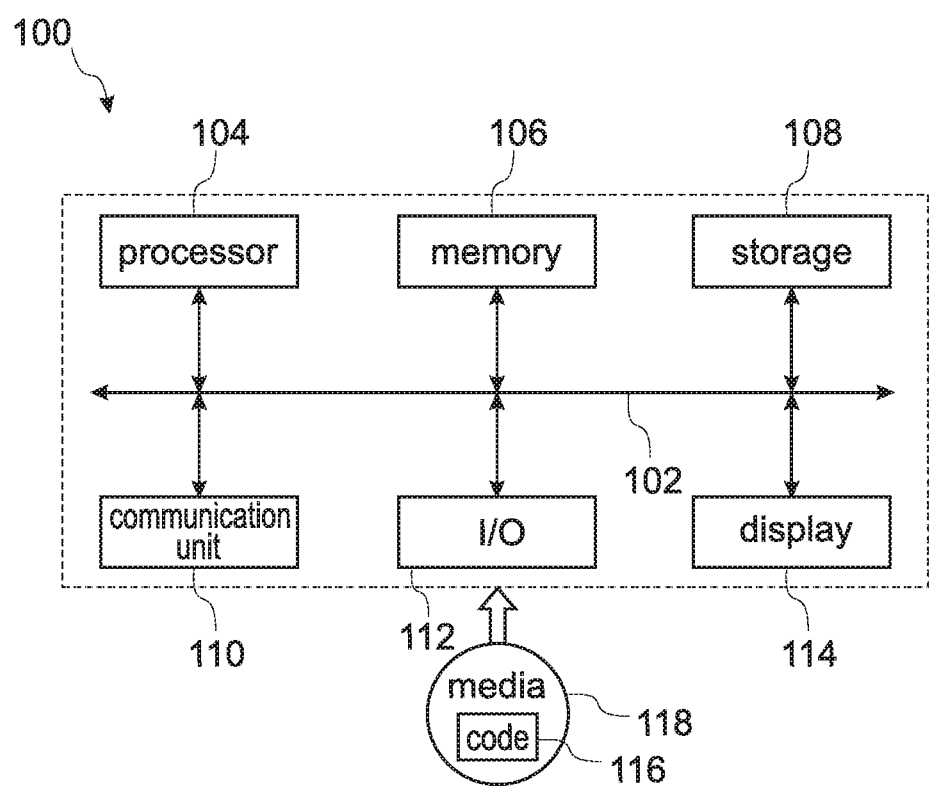
FIG. 1 is the illustration of an embodiment of a data processing system in which the computer usable program code of the computer program product in accordance with an embodiment of the present invention can be implemented.

FIG. 1 is the illustration of an embodiment of a data processing system 100 in which the computer usable program code of the computer program product in accordance with an embodiment of the present invention may be implemented.

The radiation inverse treatment planning system 100 according to the invention comprises:
  a radiation source (not visible),
  at least a data bus system 102, a memory 106 coupled to the data bus system 102, wherein the memory comprises a computer usable program code, and a processing unit 104 coupled to the data bus system 102.

Figure 2:
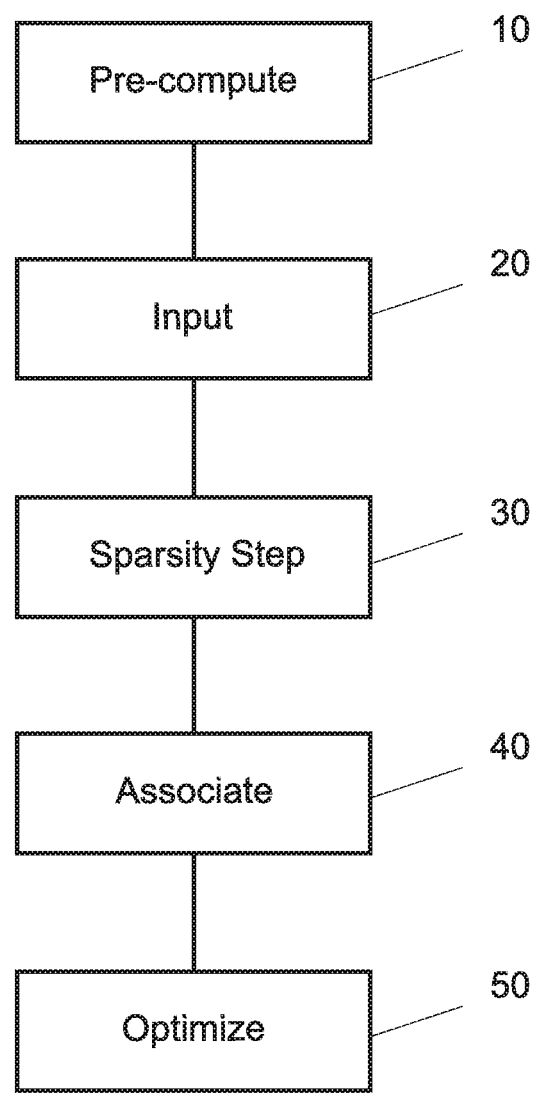
FIG. 2 shows a flow-chart representation of a method which can be implemented in an embodiment of the radiation inverse treatment planning system according to the present invention.

FIG. 2 shows a flow-chart representation of a method which can be implemented in an embodiment of the inverse treatment planning system 100 according to the present invention.

Advantageously, the processing unit 102 is configured to execute the computer usable program code to pre-compute a dictionary composed of a list (or set) of possible dose shots' locations, incidence angles, sizes and shapes (step 10), define by the user the desired dose in the target area and potential additional constraints, for instance on the areas to be protected from too high dose radiation (step 20), solve a convex problem to determine the plan, i.e. to find which of those shots, and with which weights, will be actually used (steps 30, 40 and 50).

In one preferred embodiment, the set of pre-computed dose shots (step 10) can be located on a discrete three-dimensional (3D) grid of fixed resolution in a 3D space.

As discussed, the first step of FIG. 1 (step 10) is to build a list dictionary of possible dose shots (or dose distributions patterns) located (centered) at all possible locations and incidence angles on a 3D grid, or a subset of them (e.g. those located only within the target area).

In one preferred embodiment, two consecutive locations on this grid in each of the three dimensions are spaced by a distance less than 1 mm, e.g. 0.5 mm.

The dictionary is thus the set of functions $$\{a^j\}_{j=1}^N$$

with N denoting the size of the dictionary.

Each component $a^j$ of the dictionary will be named "atom".

The complete dose distribution can be calculated as the weighted sum of the contributions from each atom. The dose d at any point (x, y, z) of the 3D space can be computed as $$d(x, y, z) = \sum_{j=1}^N s_j a^j(x, y, z)$$

where $s_j$ denotes the weight associated to the j-th atom.

For example, for a given system using a rotating gantry and a moving couch, the dictionary can be obtained by discretizing the rotation angles of the gantry and the positions of the coach to create a discrete grid on the sphere and considering different beam sizes and shapes for each discrete location and orientation.

As another example, for a given LINAC location and orientation, the beam going through a multi-leave collimator can be discretized as a series of small discrete "beamlets", parallel to each other, each of them with their own weight that has to be determined. For specific newer systems, dose rate modulation can also be discretized.

In one preferred embodiment, this step can be performed by considering pre-calculated individual dose profiles, produced by a set of individual beams with different locations, orientations, sizes and shapes, and by translating them to all the considered grid points. This step can also be performed by taking into account the physical properties of the patient's anatomy, based for instance on the medical images acquired for the planning.

The objective of the inverse planning method is to find the minimum number of non-zero weights $s_j$ so that the constraints imposed by the user at step 20 are satisfied.

The complete dose distribution d can be calculated at a predefined number of points in the 3D space, for instance on a pre-defined grid G of P points.

This dose distribution d can be represented by a vector f of dimension P that can be defined as $$f = As$$

where A is an P×N matrix whose columns are the value of the dose delivered by each atom at each point of the grid G, and s is a vector of the weights of the atoms, of dimension N.

According to the invention, s has to be sparse, i.e. the number K of non-zero coefficients of s has to be much smaller than N. In a typical example, N may be as big as 100,000 or more, while K may be as small as 50 or less.

The positions of the non-zero elements in s determine which atoms in the dictionary will be used in the treatment, i.e. they determine the actual shot shapes and their locations.

The values of s determine the shot weights.

Once building the dictionary A (step 10 in FIG. 2), a vector s with minimum number of non-zero elements is computed by satisfying the dose constraints defined by the user in step 20.

It must be understood that, even if the dose constraints in FIG. 2 are inputted by the user after the pre-computation of the dictionary, this inputting can be performed before the pre-computing step 10.

As optimization criteria, it is find a plan that minimizes a weighted L1 norm of vector s (i.e. the sum of the elements of the vector s) and meets all the dose constraints. The weighted L1 norm of s is closely related to the treatment time. This optimization problem can advantageously be formulated as a convex optimization problem (step 50), as only the weights of the individual dose shots are optimized (in fact simultaneously optimize the locations, sizes, shapes, and weights of the individual dose shots so as to guarantee a dose constraint will result in a non-convex optimization problem). In another embodiment, it is find a plan that minimizes a weighted L0 norm of vector s (i.e. the number of the elements of the vector s that are different from zero) and meets all the dose constraints. In another embodiment, it is find a plan that minimizes a weighted L2 norm of vector s and meets all the dose constraints.

Let T denote the set of indexes of the vector f corresponding to points that belong to the target region, let R denote those belonging to the sensitive areas to be protected, and Q the set of remaining indexes. Also, let $a_i$ denotes the i-th row of the matrix A. The i-th component of the vector f can be expressed as $$f_i = a_i s$$

i.e. the inner product of the i-th row of the dictionary A and the vector s. Thus, the optimal plan is computed by solving the following convex problem:

$$\min \|s\|_{1,w} \text{ such that } \begin{cases} a_i s \geq b_{min} & \forall i \in T \\ a_i s \leq b_{max} & \forall i \in R \\ a_i s \leq b_{min} & \forall i \in Q \\ s \geq 0 \end{cases}$$

where

-continued $$\|s\|_{1,w} = \sum_{i=1}^{N} w_i |s_i|$$

denotes the weighted L1 norm of the vector s with weights $w_i \geq 0$, $b_{min}$ is the minimum dose at the target region T, $b_{max}$ is the maximum allowed dose at sensitive regions R, and $s \geq 0$ denotes the positivity constraint on the values of s.

Additional constraints can be added at step 20 to the formulation as equality or inequality constraints. This can for instance be related to a desired dose gradient index, or to different values of the minimal dose delivered to different parts of the target region, or to different values of the maximal dose delivered to regions to be protected. This optimization problem can then be solved by any convex optimization method, for instance by convex linear programming algorithms.

The weighted L1 norm is a convex function that promotes sparse solutions, i.e. solving this constrained minimization problem will determine the sparsest vector s that meets all the dose constraints.

Minimizing the number of beams and the sum of their weights is akin to minimize the treatment time. Other types of convex penalties that promote structured sparsity, such as the L0, L1 or L2 norm that promotes group sparsity, can be employed. The idea behind this approach is to leverage from the particular structure of a particular LINAC technique.

This optimization problem can then be solved by any convex optimization method, for instance by convex linear programming algorithms.

The inventive system proposes then an inverse treatment planning system wherein the complete dose distribution is modeled as a sparse linear combination of single shot dose chosen from a pre-computed dictionary or library of pre-computed single shot doses.

A convex constrained optimization procedure is used to determine the treatment plan. The shot weights are optimized, under sparsity constraint, to guarantee that the constraints on the dose distribution be met.

The optimization procedure does not require the user to provide initial shot locations, and the convex optimization formulation can include dose constraints applied both to the target region and to other areas such as sensitive structures to be protected against too high dose radiation.

FIG. 1 is an embodiment of a system 100 according to the invention. The system 100 of FIG. 1 may be located and/or otherwise operate at any node of a computer network, that may exemplarily comprise clients, servers, etc., and it is not illustrated in the figure. In the embodiment illustrated in FIG. 1, the system 100 includes communications fabric 102, which provides communications between processor unit 104, memory 106, persistent storage 108, communications unit 110, input/output (I/O) unit 112, and display 114.

Processor unit 104 serves to execute instructions for software that may be loaded into memory 106. Processor unit 104 may be a set of one or more processors or may be a multi-processor core, depending on the particular implementation. Further, processor unit 104 may be implemented using one or more heterogeneous processor systems in which a main processor is present with secondary processors on a single chip. As another illustrative example, the processor unit 104 may be a symmetric multi-processor system containing multiple processors of the same type.

In some embodiments, the memory 106 shown in FIG. 1 may be a random access memory or any other suitable volatile or non-volatile storage device. The persistent storage 108 may take various forms depending on the particular implementation. For example, the persistent storage 108 may contain one or more components or devices. The persistent storage 108 may be a hard drive, a flash memory, a rewritable optical disk, a rewritable magnetic tape, or some combination of the above. The media used by the persistent storage 108 also may be removable such as, but not limited to, a removable hard drive.

The communications unit 110 shown in FIG. 1 provides for communications with other data processing systems or devices. In these examples, communications unit 110 is a network interface card. Modems, cable modem and Ethernet cards are just a few of the currently available types of network interface adapters. Communications unit 110 may provide communications through the use of either or both physical and wireless communications links.

The input/output unit 112 shown in FIG. 1 enables input and output of data with other devices that may be connected to the system 100. In some embodiments, input/output unit 112 may provide a connection for user input through a keyboard and mouse. Further, input/output unit 112 may send output to a printer. Display 114 provides a mechanism to display information to a user.

Instructions for the operating system and applications or programs are located on the persistent storage 108. These instructions may be loaded into the memory 106 for execution by processor unit 104. The processes of the different embodiments may be performed by processor unit 104 using computer implemented instructions, which may be located in a memory, such as memory 106. These instructions are referred to as program code, computer usable program code, or computer readable program code that may be read and executed by a processor in processor unit 104. The program code in the different embodiments may be embodied on different physical or tangible computer readable media, such as memory 106 or persistent storage 108.

Program code 116 is located in a functional form on the computer readable media 118 that is selectively removable and may be loaded onto or transferred to the system 100 for execution by processor unit 104. Program code 116 and computer readable media 118 form a computer program product 120 in these examples. In one example, the computer readable media 118 may be in a tangible form, such as, for example, an optical or magnetic disc that is inserted or placed into a drive or other device that is part of persistent storage 108 for transfer onto a storage device, such as a hard drive that is part of persistent storage 108. In a tangible form, the computer readable media 118 also may take the form of a persistent storage, such as a hard drive, a thumb drive, or a flash memory that is connected to the system 100. The tangible form of computer readable media 118 is also referred to as computer recordable storage media. In some instances, computer readable media 118 may not be removable.

Alternatively, the program code 116 may be transferred to the system 100 from computer readable media 118 through a communications link to communications unit 110 and/or through a connection to input/output unit 112. The communications link and/or the connection may be physical or wireless in the illustrative examples. The computer readable media also may take the form of non-tangible media, such as communications links or wireless transmissions containing the program code.

The different components illustrated for data processing system 100 are not meant to provide architectural limitations to the manner in which different embodiments may be implemented. The different illustrative embodiments may be implemented in a data processing system including components in addition to or in place of those illustrated for data processing system 100. Other components shown in FIG. 1 can be varied from the illustrative examples shown. For example, a storage device in the system 100 is any hardware apparatus that may store data. Memory 106, persistent storage 108, and computer readable media 118 are examples of storage devices in a tangible form.

According to an embodiment, the system according to the invention is implemented on a processing unit (CPU) of a single computer. In another embodiment, it is implemented on a multi-cores computer, the cores working in parallel. In another embodiment, it is implemented on a Graphic Processing Unit (GPU) of a computer. In another embodiment, it is implemented on a plurality of computers, which work totally or partially in parallel.

According to an independent aspect of the invention, the system according to the invention can be shared in innovative training scenarios (including tele-training and remote coaching). In one embodiment, the interactive inverse planning is provided as a tele-service, the system running in a processing centre accessed by the users over secured Internet connections.

REFERENCE NUMBERS USED IN THE FIGURES

10 Pre-computing step
20 User inputting step (constraints)
30 Sparsity step
40 Association step
50 Optimization step
100 System
102 Data bus system
104 Processing unit
106 Memory
108 Persistent storage
110 Communication unit
112 I/O unit
114 Display
116 Program code
118 Computer readable media

The invention claimed is:

1. A radiation inverse treatment planning system for a linear accelerator, comprising:
   a radiation source, configured for delivering individual radiotherapeutic beams, wherein the beam is comprised of a plurality of beamlets, each individual radiotherapeutic beam having a predetermined location and incidence angle inside and/or outside a target area, a size and a shape,
   at least a data bus system,
   a memory coupled to the data bus system, wherein the memory comprises a computer usable program code, and
   a processing unit coupled to the data bus system, wherein the processing unit is configured to execute the computer usable program code to
      pre-compute a dictionary composed of a set of individual possible radiotherapeutic beams including, for each individual radiotherapeutic beam its location and its incident angle,
      associate a weight to each individual radiotherapeutic beam, based on one or more constraints,
   wherein the processing unit executes the computer usable program code to
      find the sparsest subset of individual radiotherapeutic weighted beams, so as to satisfy said one or more constraints.

2. The system of claim 1, the weight associated to each individual radiotherapeutic beam comprising the time of irradiation.

3. The system of claim 1, the weight associated to each individual radiotherapeutic beam comprising the dose rate.

4. The system of claim 1, the weight associated to each individual radiotherapeutic beam comprising dose profile.

5. The system of claim 1,
   a first physical support for said radiation source,
   a second physical support arranged for receiving a patient,
   wherein the first physical support and the second physical support are arranged to be moved one relative to the other,
   and wherein the processing unit executes the computer sable program code to
   find the sparsest subset of individual radiotherapeutic beams, so as to satisfy said one or more constraints each time that the first physical support is moved relatively to the second physical support and/or each time that the second physical support is moved relatively to the first physical support.

6. The system of claim 1,
   wherein the processing unit executes the computer usable program code to
   find the sparsest subset of individual radiotherapeutic beams, so as to satisfy said one or more constraints each time that a patient and/or an organ of the patient moves.

7. The system of claim 1, wherein the processing unit executes the computer usable program code to
   find the minimum number of non-zero weights so as to satisfy said one or more constraints.

8. The system of claim 1, wherein the number of non-zero weights is at least $\frac{1}{100}$ of the number of pre-computed individual radiotherapeutic beams.

9. The system of claim 1, wherein the processing unit executes the computer usable program code to
   minimize a weighted L1 norm of the vector of weights while satisfying said one or more constraints, so as to obtain an optimal subset of individual radiotherapeutic beams.

10. The system of claim 1, wherein the processing unit executes the computer usable program code to
    minimize a weighted L0 norm of the vector of weights while satisfying said one or more constraints, so as to obtain an optimal subset of individual radiotherapeutic beams.

11. The system of claim 1, wherein the processing unit executes the computer usable program code to
    minimize a weighted L2 norm of the vector of weights while satisfying said one or more constraints, so as to obtain an optimal subset of individual radiotherapeutic beams.

12. The system of claim 1, wherein the processing unit executes the computer usable program code to
    locate each individual radiotherapeutic beam in a location of a three-dimensional grid.

13. The system of claim 1, wherein the processing unit is configured to execute the computer usable program code in real-time.

14. The system of claim 1, wherein the constraint comprises dose constraints applied to the target region and/or to other areas such as sensitive structures to be protected against too high dose radiation.

15. The system of claim 1, wherein the processing unit is configured to execute the computer usable program code to
- take into account the physical properties of the patient's anatomy during the pre-computing of the set of individual radiotherapeutic beams.

16. The system of claim 1, wherein the processing unit executes the computer usable program code to
- apply a convex optimization criterion.

17. The system of the previous claim 16, said optimization criterion comprising minimizing a treatment time.

18. The system of claim 1, wherein the radiation source is a linear accelerator.

19. The system of claim 1, wherein the radiation source is a cobalt source or a proton beam.

20. A computer program product, comprising:
- a tangible non-transitory computer usable medium including computer usable program code for a radiation inverse treatment planning system comprising a radiation source configured for delivering individual radiotherapeutic beams, wherein the beam is comprised of a plurality of beamlets, each individual radiotherapeutic beam having a predetermined location and incidence angle inside and/or outside a target area, a size and a shape, the computer usable program code being used to
- pre-compute a dictionary composed of a set of individual possible radiotherapeutic beams including for each individual radiotherapeutic beam its location and its incident angle,
- associate a weight to each individual radiotherapeutic beam, based on one or more constraints,
- wherein a processing unit executes the computer usable program code to
- find the sparsest subset of individual radiotherapeutic weighted beams so as to satisfy said one or more constraints.

21. A non-transitory computer data carrier storing presentation content created with a radiation inverse treatment planning method, comprising the following steps:
- pre-compute a dictionary composed of a set of individual radiotherapeutic beams including, for each individual radiotherapeutic beam its location and its incident angle, each individual radiotherapeutic beam being generated by a radiation source and having a predetermined location and incidence angle inside and/or outside a target area, a size and a shape, wherein the beam is comprised of a plurality of beamlets,
- associate a weight to each individual radiotherapeutic beam, based on one or more constraints,
- wherein a processing unit executes the computer usable program code to
- find the sparsest subset of individual radiotherapeutic weighted beams so as to satisfy said one or more constraints.

* * * * *